United States Patent [19]

Wangemann et al.

[11] Patent Number: 5,514,368

[45] Date of Patent: May 7, 1996

[54] PROCESS FOR THE PRODUCTION OF HYDROPHILICIZED TRIGLYCERIDES

[75] Inventors: Frank Wangemann, Solingen; Hans-Christian Raths, Monheim; Rudolf Zauns-Huber, Duesseldorf, all of Germany

[73] Assignee: Henkel Kommanditgesellschaft auf Aktien, Duesseldorf, Germany

[21] Appl. No.: 244,976

[22] PCT Filed: Dec. 8, 1992

[86] PCT No.: PCT/EP92/02835

§ 371 Date: Jun. 17, 1994

§ 102(e) Date: Jun. 17, 1994

[87] PCT Pub. No.: WO93/12215

PCT Pub. Date: Jun. 24, 1993

[30] Foreign Application Priority Data

Dec. 17, 1991 [DE] Germany ............... 41 41 532.9

[51] Int. Cl.$^6$ ................ A61K 7/06; C11D 1/28
[52] U.S. Cl. ............. 424/70.1; 554/98; 554/149; 424/401; 252/89.1
[58] Field of Search ............. 424/70.1, 98; 554/49

[56] References Cited

U.S. PATENT DOCUMENTS 4,975,090  12/1990  Brehm et al. ............. 8/94.22

FOREIGN PATENT DOCUMENTS

| 0247509 | 12/1987 | European Pat. Off. . |
| 0305925 | 3/1989 | European Pat. Off. . |
| 0353704 | 2/1990 | European Pat. Off. . |
| 3432219 | 3/1986 | Germany . |
| 3941365 | 6/1991 | Germany . |
| 9106531 | 5/1991 | WIPO . |
| 9106532 | 5/1991 | WIPO . |
| 9209570 | 6/1992 | WIPO . |

OTHER PUBLICATIONS

J. Falbe (ed.), "Surfactants in Consumer Products", Springer Verlag, Berlin–Heidelberg, 1987, p. 61.

*Primary Examiner*—Jyothsan Venkat
*Attorney, Agent, or Firm*—Ernest G. Szoke; Wayne C. Jaeschke; Daniel S. Ortiz

[57] ABSTRACT

The invention is a process for hydrophilicizing a mixture of triglycerides and glycerol by ethoxylation of the mixture followed by sulfonation with sulfur trioxide and neutralization.

14 Claims, No Drawings

PROCESS FOR THE PRODUCTION OF HYDROPHILICIZED TRIGLYCERIDES

FIELD OF THE INVENTION

This invention relates to a process for the production of hydrophilicized triglycerides, in which saturated, unsaturated and/or blown triglycerides are ethoxylated, sulfonated and neutralized, and to the use of these products in surface-active preparations.

RELATED ART

Hydrophilicized triglycerides are known surface-active compounds which may be prepared by sulfonation and/or ethoxylation of glycerides.

According to European patent application EP 0 305 925 A1, for example, epoxidized ricinolglycerides are reacted with gaseous sulfur trioxide.

According to German patent application DE 39 41 365 A1 and to International patent application WO 91/06532, surface-active substances can be obtained by sulfonating saturated or unsaturated triglycerides with gaseous sulfur trioxide.

In addition, European patent application EP 0 247 509 A1 describes leather oiling preparations which are produced by initially ethoxylating and/or epoxidizing unsaturated triglycerides and then sulfating the resulting intermediate products with sulfuric acid.

German patent application DE 34 32 219 A1 describes perfume oil solubilizers obtainable by subjecting epoxidized triglycerides to ring opening with nucleophiles and then ethoxylating the resulting polyols. Finally, International patent application WO 91/06531 describes the sulfation of these products.

Overall, the processes mentioned above have major disadvantages which are an obstacle to production of the products on an industrial scale:

Triglycerides which are hydrophilicized either by sulfonation or by ethoxylation show inadequate solubility in water for many applications.

The addition of sulfuric acid onto the double bonds of unsaturated, optionally ethoxylated triglycerides can only be successfully accomplished if the sulfating agent is used in excess and is attended by serious technical problems through the increase in viscosity. The subsequent neutralization of the acidic products leads inevitably to an undesirably high salt burden on account of the excess of sulfuric acid.

Epoxidized triglycerides can only be obtained at considerable expense and, hence, are unsuitable as raw materials for the production of hydrophilicized triglycerides on economic grounds.

Accordingly, the problem addressed by the present invention was to develop a new process for the production of hydrophilicized triglycerides which would not be attended by any of the disadvantages mentioned above.

BRIEF SUMMARY OF THE INVENTION

The present invention relates to a process for the production of hydrophilicized triglycerides which is characterized in that saturated, unsaturated and/or blown triglycerides corresponding to formula (I):

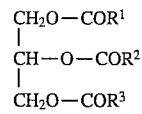

in which $R^1CO$, $R^2CO$ and $R^3CO$ independently of one another represent optionally hydroxy-substituted acyl radicals containing 6 to 24 carbon atoms and 0 or 1 to 5 double bonds, a) are reacted with ethylene oxide in the presence of glycerol and alkaline catalysts, b) the resulting ethoxylated triglycerides are sulfonated with gaseous sulfur trioxide and c) the resulting acidic sulfonation products are subsequently neutralized with aqueous bases.

It has surprisingly been found that ethoxylated triglycerides may even be continuously sulfonated with gaseous sulfur trioxide without any viscosity problems.

DETAILED DESCRIPTION OF THE INVENTION

By triglycerides are meant full esters of glycerol with three identical or even different fatty acids. Triglycerides with iodine values of 7 to 180 and, more particularly, 80 to 115 are preferably used as raw materials.

The fatty acid component of the triglycerides may be derived, for example, from the following fatty acids: caproic acid, caprylic acid, capric acid, lauric acid, myristic acid, palmitic acid, palmitoleic acid, stearic acid, oleic acid, elaidic acid, petroselic acid, linoleic acid, linolenic acid, ricinoleic acid, arachic acid, gadoleic acid, behenic acid, erucic acid, arachidonic acid and clupanodonic acid. Triglycerides corresponding to formula (I), in which $R^1CO$, $R^2CO$ and $R_3CO$ independently of one another represent acyl radicals containing 16 to 18 carbon atoms and 0 or 1 or 2 double bonds, are preferably used.

The triglycerides may be of synthetic origin. However, it is preferred to use natural starting materials, for example palm oil, palm kernel oil, coconut oil, olive oil, rapeseed oil from old and new plants, sunflower oil from old and new plants, linseed oil, peanut oil, cottonseed oil, coriander oil, meadowfoam oil, lard oil, lard, beef tallow and fish oil. So-called "blown oils" are also suitable as starting products. Blown oils are autoxidized triglycerides which are obtained by blowing air heated to 100° to 150° C. into fatty oils [Römpp, Chemielexikon, Thieme Verlag, Stuttgart, 1990, page 1498].

From their raw materials, the triglycerides may contain proportions of partial glycerides providing they do not exceed 50% by weight.

The ethoxylation of the triglycerides may be carried out by methods known per se. Suitable alkaline catalysts are alkali metal hydroxides, alkaline earth metal hydroxides and/or alkali metal $C_{1-4}$ alcoholates. Typical examples are potassium hydroxide, barium hydroxide, potassium tert.butylate and, in particular, sodium hydroxide and sodium methylate. The ethoxylation may typically be carried out in the presence of 0.1 to 2% by weight, based on triglyceride, of the alkaline catalysts. To accelerate the reaction, glycerol is added to the triglycerides in quantities of 0.5 to 5% by weight and preferably in quantities of 1.5 to 3.0% by weight, based on triglyceride. The ethoxylation is advantageously carried out at temperatures of 150° to 180° C. and, more particularly, at temperatures of 160° to 170° C. and under autogenous pressures of 1 to 5 bar and more particularly 2 to 4 bar.

The molar ratio in which the triglycerides and the ethylene oxide are used may be from 1:0.8 to 1:50 and is preferably from 1:1 to 1:10. In the ethoxylation reaction, the ethylene oxide is inserted into the carbonyl ester bonds under statistical laws. Accordingly, the degree of ethoxylation calculable from the molar ratio is only an average value.

The sulfonation of the ethoxylated triglycerides with gaseous sulfur trioxide may be carried out by the known method used for fatty acid lower alkyl esters [J. Falbe (ed.), "Surfactants in Consumer Products", Springer Verlag, Berlin-Heidelberg, 1987, page 61], preferably using reactors operating on the falling film principle. The sulfur trioxide is diluted with an inert gas, preferably air or nitrogen, and used in the form of a gas mixture containing the sulfonating agent in a concentration of 1 to 8% by volume and, more particularly, in a concentration of 2 to 5% by volume.

The ethoxylated triglycerides and the sulfur trioxide may be used in a molar ratio of 1:0.3 to 1:3.0, preferably in a molar ratio of 1:0.9 to 1:2.5 and more preferably in a molar ratio of 1:1.0 to 1:2. The objective may even be to sulfonate only part, for example 10 to 25%, rather than all of the double bonds present in the molecule. It has proved to be optimal for this purpose to carry out the sulfonation with a molar ratio of 1:1 to 1:1.2. Taking the viscosity of the reaction products into account, the sulfonation may be carried out at temperatures of 30° to 90° C., temperatures in the range from 50° to 80° C. having proved to be optimal.

For neutralization, the acidic sulfonation products accumulating in the sulfonation of the ethoxylated triglycerides are stirred into aqueous bases and adjusted to a pH value of 6.5 to 8.5. Suitable neutralization bases are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and also primary, secondary or tertiary $C_{1-4}$ alkylamines. The neutralization bases are preferably used in the form of 5 to 55% by weight aqueous solutions, 5 to 25% by weight aqueous sodium hydroxide solutions being preferred.

To improve the pH stability and storage stability of the products, it is advisable to carry out the neutralization with an excess of 10 to 20 mole-% of the base, based on acidic reaction product, at temperatures in the range from 70° to 90° C. In addition, to improve the degree of sulfonation, it has proved to be of advantage to subject the acidic reaction product after leaving the reactor and before the neutralization step to an after-reaction for 0.1 to 1 h at a temperature in the range from 70° to 90° C. This may be done, for example, discontinuously in a tank reactor or continuously in a pipe coil.

The hydrophilicized triglycerides are complex mixtures which, in addition to ethoxylated mono-, di- and triglyceride sulfonates with an internal sulfonic acid group, also contain inter alia sulfonated fatty acid ethoxylates, glyceride ether sulfates, glycerol ether sulfates, glycerol and soaps.

After neutralization, the reaction products may be bleached in known manner in the presence of hydrogen peroxide or sodium hypochlorite solution, optionally with addition of bleaching boosters, such as magnesium ions for example. Based on the solids content of the solution of sulfonation products, quantities of 0.2 to 2% by weight of hydrogen peroxide, expressed as 100% substance, or corresponding quantities of sodium hypochlorite are used for this purpose. The pH value of the solutions may be kept constant using suitable buffers, for example sodium phosphate or citric acid. In addition, it is advisable to add preservatives, for example formaldehyde solution, p-hydroxybenzoate, sorbic acid or other known preservatives, for stabilization against bacterial contamination.

The hydrophilicized triglycerides obtainable by the process according to the invention have surface-active properties, are readily soluble in water, promote the emulsification of otherwise immiscible substances and may readily be made up.

Accordingly, the present invention also relates to the use of the products for the production of laundry detergents, dishwashing detergents or cleaning products, leather oiling agents and hair-care and personal hygiene products, in which they may be present in quantities of 0.1 to 25% by weight and preferably in quantities of 1 to 10% by weight, based on the particular product.

EXAMPLES

Examples 1 to 4

I. Ethoxylation:

A mixture of 889 g (1.0 mole) of rapeseed oil from new plants (oleic acid content>80% by weight, iodine value 108), 20 g (0.2 mole) of glycerol and 4 g of sodium methylate in the form of a 30% by weight solution in methanol was introduced into a 2 liter steel autoclave. The pressure vessel was alternately evacuated and purged with nitrogen three times, closed and then heated to a temperature of 175° C. 44 to 220 g (1 to 5 moles) of ethylene oxide were then introduced in portions by siphon over a period of 0.5 to 2 h, an autogenous pressure of 4 bar being established. After the addition, the mixture was left to after-react for another 0.5 h, after which the autoclave was cooled and vented. The ethoxylated rapeseed oil was obtained in a substantially quantitative yield as a light yellow, low-viscosity liquid.

II. Sulfonation:

In a continuous falling film reactor (length 120 cm, cross-section 1 cm, educt throughput 600 g/h) with jacket cooling and a side inlet for $SO_3$ gas, 5 moles of ethoxylates A1 to A4 were reacted with 480 g (6 moles) of gaseous sulfur trioxide (5% by volume in air)—corresponding to a molar ratio of ethoxylate to $SO_3$ of 1:1.2—at a temperature $T^1$ of 75° C. The acidic sulfonation products were continuously introduced into a 37% by weight aqueous sodium hydroxide solution at a temperature $T^2$ of 80° C. and neutralized at pH=7.5. The products were obtained in the form of low-viscosity opaque liquids. The results are set out in Table 1.

TABLE 1

| | Hydrophilicized triglycerides Percentages as % by weight | | | | | | |
|---|---|---|---|---|---|---|---|
| | Ethoxylation | | | Sulfonation | | | |
| Ex | Eth. | EO | t(Eth) h | WAS mEg/g | US % | $SO_4^{2-}$ | $H_2O$ |
| 1 | A1 | 1 | 0.5 | 0.034 | 35.6 | 0.7 | 47.7 |
| 2 | A2 | 2 | 1.0 | 0.030 | 33.3 | 0.7 | 50.3 |
| 3 | A3 | 3 | 1.5 | 0.027 | 31.4 | 0.5 | 50.8 |
| 4 | A4 | 5 | 2.0 | 0.023 | 28.3 | 0.6 | 51.5 |

Legend:
Eth. = ethylene oxide adduct

TABLE 1-continued

| | | | Hydrophilicized triglycerides Percentages as % by weight | | | | |
| --- | --- | --- | --- | --- | --- | --- | --- |
| | | Ethoxylation | | Sulfonation | | | |
| Ex | Eth. | EO | t(Eth) h | WAS mEg/g | US % | $SO_4^{2-}$ | $H_2O$ |

EO = average degree of ethoxylation
t(Eth) = ethoxylation time

The content of washing-active substance (WAS) and the unsulfonated components (US) were determined in accordance with DGF-Einheitsmethoden, Stuttgart, 1950–1984, H-III-10 and G-II-6b. The sulfate content was expressed as sodium sulfate, the water content was determined by the Fischer method.

We claim:

1. A process for the production of hydrophilicized triglycerides, which comprises:

a) reacting at least one unsaturated triglyceride having an iodine value of from 80 to 180, of the formula:

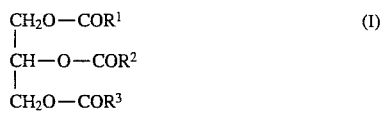

wherein $R^1CO$, $R_2CO$ and $R_3CO$ independently of one another represent optionally hydroxy-substituted acyl radicals having 6 to 24 carbon atoms and up to 5 double bonds, with ethylene oxide in the presence of glycerol and an alkaline catalyst to form an ethoxylated triglyceride mixture;

b) sulfonating the ethoxylated triglyceride mixture with gaseous sulfur trioxide to form a sulfonated mixture; and c) neutralizing the sulfonated mixture with an aqueous base.

2. A process of claim 1, wherein $R^1CO$, $R^2CO$ and $R^3CO$ independently of one another represent acyl radicals having 16 to 18 carbon atoms and up to 2 double bonds.

3. A process of claim 1 wherein the triglycerides have an iodine value of 80 to 115.

4. A process of claim 1 wherein the alkaline catalyst comprises at least one member selected from the group consisting of alkali metal hydroxides, alkaline earth metal hydroxides and alkali metal $C_{1-4}$ alcoholates.

5. A process of claim 1 wherein the alkaline catalyst is present from 0.1 to 2% by weight, of the triglyceride.

6. A process of claim 1 wherein the glycerol is present from 0.5 to 5% by weight, of the triglyceride.

7. A process of claim 1 wherein the triglycerides are reacted with the ethylene oxide in a molar ratio of 1:0.8 to 1:50.

8. A process of claim 1 wherein the triglycerides are reacted with ethylene oxide at a temperature of 150° to 180° C. under an autogenous pressure of 1 to 5 bar.

9. A process of claim 1 wherein a molar ratio of ethoxylated triglycerides to sulfur trioxide is from 1:0.3 to 1:3.0.

10. A process of claim 1 wherein the sulfonation is carried out at a temperature of 30° to 90° C.

11. A process of claim 1 wherein the sulfonation is carried out continuously in a falling film reactor.

12. A process of claim 1 wherein the neutralization is carried out with a 5 to 55% by weight aqueous composition comprising at least one base selected from the group consisting of alkali metal hydroxides, alkaline earth metal oxides, alkaline earth metal hydroxides, ammonia, $C_{2-4}$ mono-alkanolamines, $C_{2-4}$ dialkanolamines, $C_{2-4}$ trialkanolamines, $C_{1-4}$ alkyl primary amines, $C_{1-4}$ alkyl secondary amines, and $C_{1-4}$ alkyl tertiary amines.

13. A process of claim 1 wherein the pH is at 6.5 to 8.5 during the neutralization.

14. A composition selected from the group consisting of laundry detergents, dishwashing detergents, cleaning products, hair care products and personal hygiene products containing the hydrophilicized triglycerides of claim 1.

* * * * *